US010085611B2

(12) United States Patent
Yabe et al.

(10) Patent No.: US 10,085,611 B2
(45) Date of Patent: Oct. 2, 2018

(54) LIGHT SOURCE APPARATUS FOR DRIVING LIGHT SOURCES BASED ON GENERATED LIGHT ADJUSTMENT INFORMATION

(71) Applicant: OLYMPUS CORPORATION, Tokyo (JP)

(72) Inventors: Yusuke Yabe, Chofu (JP); Tomoya Takahashi, Hachioji (JP); Kotaro Ogasawara, Tokyo (JP); Satoshi Tanaka, Hino (JP); Aiko Sakai, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 359 days.

(21) Appl. No.: 14/919,849

(22) Filed: Oct. 22, 2015

(65) Prior Publication Data

US 2016/0037999 A1    Feb. 11, 2016

Related U.S. Application Data

(63) Continuation of application No. PCT/JP2014/068041, filed on Jul. 7, 2014.

(30) Foreign Application Priority Data

Jul. 11, 2013  (JP) ................................. 2013-145726

(51) Int. Cl.
*A61B 1/06* (2006.01)
*A61B 1/00* (2006.01)
(Continued)

(52) U.S. Cl.
CPC ........ *A61B 1/00006* (2013.01); *A61B 1/0002* (2013.01); *A61B 1/00009* (2013.01);
(Continued)

(58) Field of Classification Search
CPC ......... A61B 1/05; A61B 1/063; A61B 1/0638; A61B 1/0653; A61B 1/07; A61B 5/0071; A61B 5/0084; A61B 5/0086
See application file for complete search history.

(56) References Cited

U.S. PATENT DOCUMENTS 6,389,205 B1   5/2002  Muckner et al.
7,179,222 B2 * 2/2007  Imaizumi ........... A61B 1/00009
                                                      600/109
(Continued)

FOREIGN PATENT DOCUMENTS

EP   2452611 A1    5/2012
EP   2 702 928 A1  3/2014
(Continued)

OTHER PUBLICATIONS

International Search Report dated Oct. 7, 2014 issued in PCT/JP2014/068041.
(Continued)

Primary Examiner — John P Leubecker
Assistant Examiner — Arnaldo Torres Diaz
(74) Attorney, Agent, or Firm — Scully, Scott, Murphy & Presser, P.C.

(57) ABSTRACT

A light source apparatus includes: a control section that acquires information relating to a ratio of a light amount value for light with second wavelength band to a light amount value for light with first wavelength band, obtains a light amount value for the light with the first wavelength band so that an observation image has a predetermined brightness, and, from the information relating to the ratio, determines a light amount value for the light with the second wavelength band, and generates light adjustment information for making first and second semiconductor light sources emit light with the light amount value for the light with the first wavelength band and the light amount value for the light (Continued)

with the second wavelength band; and a drive section that, based on the light adjustment information generated by the control section, drives the first and second semiconductor light sources.

11 Claims, 8 Drawing Sheets

(51) Int. Cl.
    *A61B 1/045*     (2006.01)
    *G02B 23/24*     (2006.01)
    *G02B 27/14*     (2006.01)
    *G02B 19/00*     (2006.01)
(52) U.S. Cl.
    CPC ............ *A61B 1/045* (2013.01); *A61B 1/0638* (2013.01); *A61B 1/0669* (2013.01); *A61B 1/0684* (2013.01); *G02B 19/0061* (2013.01); *G02B 23/2469* (2013.01); *G02B 27/141* (2013.01)

(56) References Cited

U.S. PATENT DOCUMENTS

| | | | | |
|---|---|---|---|---|
| 7,232,410 B2* | 6/2007 | Takahashi | ............ | A61B 1/0638 348/69 |
| 7,892,169 B2* | 2/2011 | Gono | ................. | A61B 1/0638 348/70 |
| 8,231,526 B2* | 7/2012 | Yabe | ................. | A61B 1/00009 600/160 |
| 8,803,056 B2* | 8/2014 | Shirota | ................. | G02B 23/26 250/205 |
| 8,936,548 B2* | 1/2015 | Ozawa | ................. | A61B 1/0638 600/178 |
| 9,072,453 B2* | 7/2015 | Kaku | ................. | A61B 1/00009 |
| 9,107,268 B2* | 8/2015 | Kubo | .................... | A61B 1/045 |
| 2003/0007087 A1* | 1/2003 | Hakamata | ............ | A61B 1/0638 348/370 |
| 2004/0122291 A1* | 6/2004 | Takahashi | ............ | A61B 1/0638 600/180 |
| 2004/0148141 A1* | 7/2004 | Tsujita | ............... | A61B 1/00009 702/190 |
| 2005/0288553 A1* | 12/2005 | Sugimoto | ............ | A61B 1/0005 600/118 |
| 2006/0109546 A1* | 5/2006 | Namba | ............... | G01N 21/6458 359/385 |
| 2006/0235277 A1* | 10/2006 | Ohkubo | ............... | A61B 1/0653 600/179 |
| 2007/0153542 A1* | 7/2007 | Gono | ................... | A61B 1/0638 362/574 |
| 2007/0213592 A1* | 9/2007 | Yamada | ............. | A61B 1/00096 600/178 |
| 2008/0039696 A1* | 2/2008 | Kamihara | .......... | G02B 23/2423 600/181 |
| 2008/0039697 A1* | 2/2008 | Morishita | .............. | A61B 1/043 600/181 |
| 2008/0051632 A1* | 2/2008 | Ito | ........................ | A61B 1/0607 600/114 |
| 2008/0239070 A1* | 10/2008 | Westwick | .............. | A61B 1/045 348/68 |
| 2008/0306343 A1* | 12/2008 | Yamazaki | .......... | A61B 1/00009 600/180 |
| 2009/0036743 A1* | 2/2009 | Yabe | .................. | A61B 1/00009 600/180 |
| 2009/0065679 A1* | 3/2009 | Tanimoto | .................. | H04N 5/33 250/208.1 |
| 2010/0016669 A1* | 1/2010 | Takaoka | ................. | A61B 1/043 600/160 |
| 2010/0094136 A1* | 4/2010 | Nakaoka | ................. | A61B 1/043 600/477 |
| 2010/0256504 A1* | 10/2010 | Moreau-Gaudry | ......................... | A61B 5/0066 600/476 |
| 2012/0053434 A1* | 3/2012 | Saito | .................. | A61B 1/00009 600/324 |
| 2012/0123213 A1 | 5/2012 | Seto | | |
| 2013/0041218 A1* | 2/2013 | Iida | ...................... | A61B 1/0638 600/109 |
| 2013/0096376 A1 | 4/2013 | Takei et al. | | |
| 2013/0148345 A1* | 6/2013 | Yabe | .................... | A61B 1/0638 362/231 |
| 2013/0286176 A1* | 10/2013 | Westwick | .............. | A61B 1/045 348/70 |
| 2015/0216400 A1* | 8/2015 | Iida | ...................... | A61B 1/0638 600/109 |
| 2016/0249019 A1* | 8/2016 | Westwick | .............. | A61B 1/045 |

FOREIGN PATENT DOCUMENTS

| | | |
|---|---|---|
| EP | 2 733 515 A1 | 5/2014 |
| JP | 2010-158413 A | 7/2010 |
| JP | 2010-158415 A | 7/2010 |
| JP | 2012-010962 A | 1/2012 |
| JP | 2012-105784 A | 6/2012 |
| JP | 2013-020814 A | 1/2013 |
| JP | 2013-111179 A | 6/2013 |
| JP | 2013-202166 A | 10/2013 |
| WO | WO 2012/108420 A1 | 8/2012 |
| WO | 2015/005277 A1 | 1/2015 |

OTHER PUBLICATIONS

Japanese Office Action dated Mar. 17, 2015 issued in JP 2015-502013.
Extended Supplementary European Search Report dated Feb. 13, 2017 in related European Patent Application No. 14 82 3176.4.

* cited by examiner (a)

(b)

LIGHT SOURCE APPARATUS FOR DRIVING LIGHT SOURCES BASED ON GENERATED LIGHT ADJUSTMENT INFORMATION

CROSS REFERENCE TO RELATED APPLICATION

This application is a continuation application of PCT/JP2014/068041 filed on Jul. 7, 2014 and claims benefit of Japanese Application No. 2013-145726 filed in Japan on Jul. 11, 2013, the entire contents of which are incorporated herein by this reference.

BACKGROUND OF INVENTION

1. Field of the Invention

The present invention relates to a light source apparatus that is suitable for an endoscope.

2. Description of the Related Art

Conventionally, endoscopes configured so that an elongated endoscope is inserted into, e.g., a body cavity to perform observation of a site to be examined and/or various treatments have widely been used. In such endoscopes, a light source apparatus for shooting an image of the inside of a cavity is employed. In recent years, a light source apparatus employing semiconductor light sources such as LEDs as light emission sections has been sometimes used. Such light source apparatus can perform light adjustment control of the LEDs by means of PWM control in which duty ratios of respective drive pulses are varied and/or current control in which LED currents are varied.

Examples of such light source apparatus using LED light sources include an apparatus disclosed in International Publication No. WO2012/108420 (hereinafter referred to as Literature 1). The apparatus in Literature 1 employs a combination of a white LED and a violet LED, enabling normal observation (white light imaging: WLI) using white light illumination and special light observation such as narrow-band observation (narrow band imaging: NBI) using violet light illumination.

SUMMARY OF THE INVENTION

A light source apparatus according to the present invention includes: a first semiconductor light source that emits light with a first wavelength band; a second semiconductor light source that emits light with a second wavelength band that is different from the first wavelength band; a control section that acquires information relating to a ratio of a light amount value for the light with the second wavelength band to a light amount value for the light with the first wavelength band, the information being provided for setting a light amount value for the light with the second wavelength band based on a light amount value for the light with the first wavelength band, obtains a light amount value for the light with the first wavelength band so that an observation image generated by an endoscope for observing a subject to which the light with the first wavelength band and the light with the second wavelength band are applied has a predetermined brightness, and, from the obtained light amount value for the light with the first wavelength band and the information relating to the ratio, determines a light amount value for the light with the second wavelength band relative to the light amount value for the light with the first wavelength band, and generates light adjustment information for making the first semiconductor light source and the second semiconductor light source emit light with the light amount value for the light with the first wavelength band and the light amount value for the light with the second wavelength band; and a drive section that, based on the light adjustment information generated by the control section, drives the first semiconductor light source and the second semiconductor light source.

DETAILED DESCRIPTION OF THE PREFERRED EMBODIMENT(S)

Embodiments of the present invention will be described below with reference to the drawings.

First Embodiment

Figure 1:
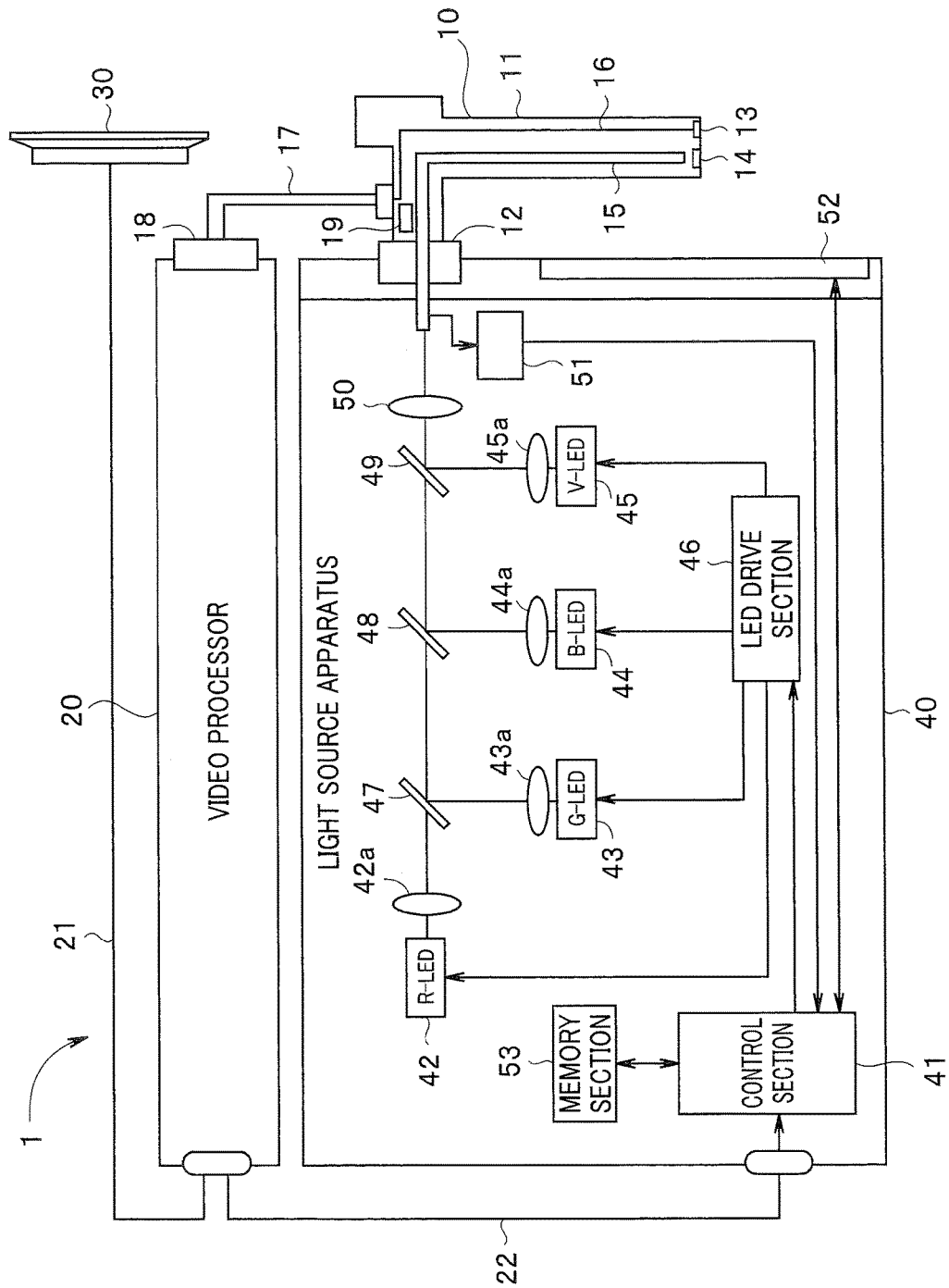
FIG. 1 is a block diagram illustrating a light source apparatus according to a first embodiment of the present invention.

FIG. 1 is a block diagram illustrating a light source apparatus according to a first embodiment of the present invention. In the present embodiment, a light source apparatus is employed in an endoscope system including an endoscope, a video processor and a monitor.

An endoscope system 1 includes an endoscope 10, a video processor 20, a monitor 30 and a light source apparatus 40. The endoscope 10 includes an elongated insertion portion 11 on the distal end side, the insertion portion 11 being able to be inserted into, e.g., a lumen, and the proximal end side of the endoscope 10 is detachably connected to the light source apparatus 40 via a connector 12.

Also, the endoscope 10 is detachably connected to the video processor 20 via a cable 17 and a connector 18. As described above, the light source apparatus 40 and the video processor 20 allow any of different types of endoscopes to be attached thereto.

At a distal end of the insertion portion 11, an image pickup device 13 for picking up a video image of an object such as the inside of a lumen and a lens 14 for applying light from the light source apparatus 40 to the object are disposed. The lens 14 allows illuminating light transmitted from the light source apparatus 40 via a light guide 15 to be applied to the object. The image pickup device 13 includes, e.g., a CCD or a CMOS sensor, and upon receipt of return light incident on an image pickup surface thereof from the object, performs photoelectric conversion of the incident object optical image and sequentially provides a picked-up image output based on accumulated charge.

The image pickup device 13 operates upon supply of drive signals including a synchronization signal from the video processor 20, and supplies a picked-up image output to the video processor 20 via a signal wire 16.

Note that the image pickup device 13 has predetermined spectral sensitivity characteristics. Characteristics of images picked up by endoscopes are different depending on the respective endoscopes mainly because of the effect of the spectral sensitivity characteristics of the respective image pickup devices. In the endoscope 10, a storage section 19 that stores scope information including information on such spectral sensitivity characteristic of the relevant endoscope. Connecting the endoscope 10 to the light source apparatus 40 via the connector 12 enables acquisition of the scope information by the light source apparatus 40.

The video processor 20 subjects predetermined signal processing to the picked-up image output to generate a video signal that can be displayed on the monitor 30. The video signal from the video processor 20 is supplied to the monitor 30 via a cable 21. Consequently, an endoscopic image that is based on the picked-up image output can be displayed on a display screen of the monitor 30.

Also, the video processor 20 can control the light source apparatus 40 so that a brightness of the picked-up image reaches a target brightness. The video processor 20 outputs information on a ratio between a brightness acquired from the picked-up image and the target brightness to the light source apparatus 40 as brightness control information. The brightness control information is supplied to a control section 41 in the light source apparatus 40 via a cable 22.

The light source apparatus 40 includes an LED (R-LED) 42 that produces red light, an LED (G-LED) 43 that produces green light, an LED (B-LED) 44 that produces blue light and a LED (V-LED) 45 that produces violet light. Although the present embodiment will be described in terms of an example in which LEDs that produce light of four colors are employed, the kinds and the number of colors are not limited to those in the present embodiment. In the present embodiment, it is only necessary that plural kinds of LEDs be used, and for example, an LED that produces amber light may be added to FIG. 1.

On respective optical axes of light emitted by the LEDs 42 to 45, lenses 42a to 45a are arranged, respectively. The respective lenses 42a to 45a convert light beams emitted by the LEDs 42 to 45 into substantially-parallel light beams and output the substantially-parallel light beams, respectively. On the optical axis of the lens 42a that outputs light from the R-LED 42, dichroic filters 47 to 49, which are included in an optical path portion, are arranged. The dichroic filter 47 also receives light from the G-LED 43 via the lens 43a. The dichroic filter 48 also receives light from the B-LED 44 via the lens 44a, and the dichroic filter 49 also receives light from the V-LED 45 via the lens 45a.

The dichroic filter 47 reflects light from the G-LED 43 and transmits light from the R-LED 42. The dichroic filter 48 reflects light from the B-LED 44 and transmits light transmitted by the dichroic filter 47. The dichroic filter 49 reflects light from the V-LED 45 and transmits light transmitted by the dichroic filter 48.

Consequently, the light beams from the LEDs 42 to 45 are combined by the dichroic filters 47 to 49. The combination light from the dichroic filter 49 enters the light guide 15 via a lens 50. Note that although the order of arrangement of the LEDs 42 to 45 may be changed by arbitrarily setting characteristics of the dichroic filters 47 to 49, arranging the LEDs 42 to 45 in order of wavelength bands of emitted light makes setting of the characteristics of the dichroic filters easier.

The LEDs 42 to 45 are driven by an LED drive section 46 and thereby turned on. The LED drive section 46 is controlled by the control section 41 so as to generate PWM pulses, which form drive signals for driving the respective LEDs. Note that each of the LEDs 42 to 45 is configured to emit light in an amount according to a duty ratio and a current amount of PWM pulses from the LED drive section 46. The control section 41 outputs light adjustment information for controlling the respective LEDs 42 to 45 to the LED drive section 46, thereby controlling the duty ratios and the current levels of the PWM pulses to perform light adjustment control of the respective LEDs 42 to 45.

The control section 41 generates the light adjustment information so that a predetermined color balance can be maintained among the amounts of light emitted by the respective LEDs 42 to 45. The color balance among the respective LEDs 42 to 45 needs to be determined by the spectral sensitivity characteristics of the endoscope 10. Upon the endoscope 10 being connected to the light source apparatus 40 via the connector 12, a reading section 51 provided in the light source apparatus 40 reads the scope information recorded in the storage section 19 and outputs the scope information to the control section 41. The control section 41 determines a ratio among the amounts of light emitted by the respective LEDs 42 to 45 (light amount ratio) based on the scope information, and controls the amounts of light emitted by the respective LEDs 42 to 45 so that the light amount ratio is maintained.

Note that although the above description has been provided in terms of the case where the storage section 19 keeps information on the spectral sensitivity characteristics of the image pickup device, the storage section 19 may store information on a ratio of amounts of light emitted by the LEDs 42 to 45 based on the spectral sensitivity characteristics.

Note that, in order to obtain an optimum color balance, it is only necessary to input information on the spectral sensitivity characteristics of the endoscope 10 to the control section 41, and it is not necessarily required to provide the storage section 19 and the reading section 51. The light source apparatus 40 is provided with an operation panel 52, and the operation panel 52 can output a signal that is based on an operation performed by a user to the control section 41. Use of the operation panel 52 enables input of information on the spectral sensitivity characteristics of the endoscope 10. Also, a non-illustrated display section is provided in the operation panel 52, enabling display of, e.g., present setting values.

The control section 41 controls the amounts of light from the respective LEDs 42 to 45 while maintaining a light amount ratio providing an optimum color balance based on the brightness control information from the video processor 20. For example, the control section 41 obtains light adjustment information for an amount of light from the G-LED 43 that should be set according to the brightness control information, and obtains light adjustment information so as to achieve the light amount ratio that is based on the scope information, for each of the other LEDs 42, 44 and 45. The memory section 53 stores a table in which the light adjustment information for the amount of light from the G-LED 43 that should be set according to the brightness control information is written, and the control section 41 reads light adjustment information stored in the memory section 53, based on the brightness control information, and thereby can acquire light adjustment information for controlling the G-LED 43.

Figure 2:
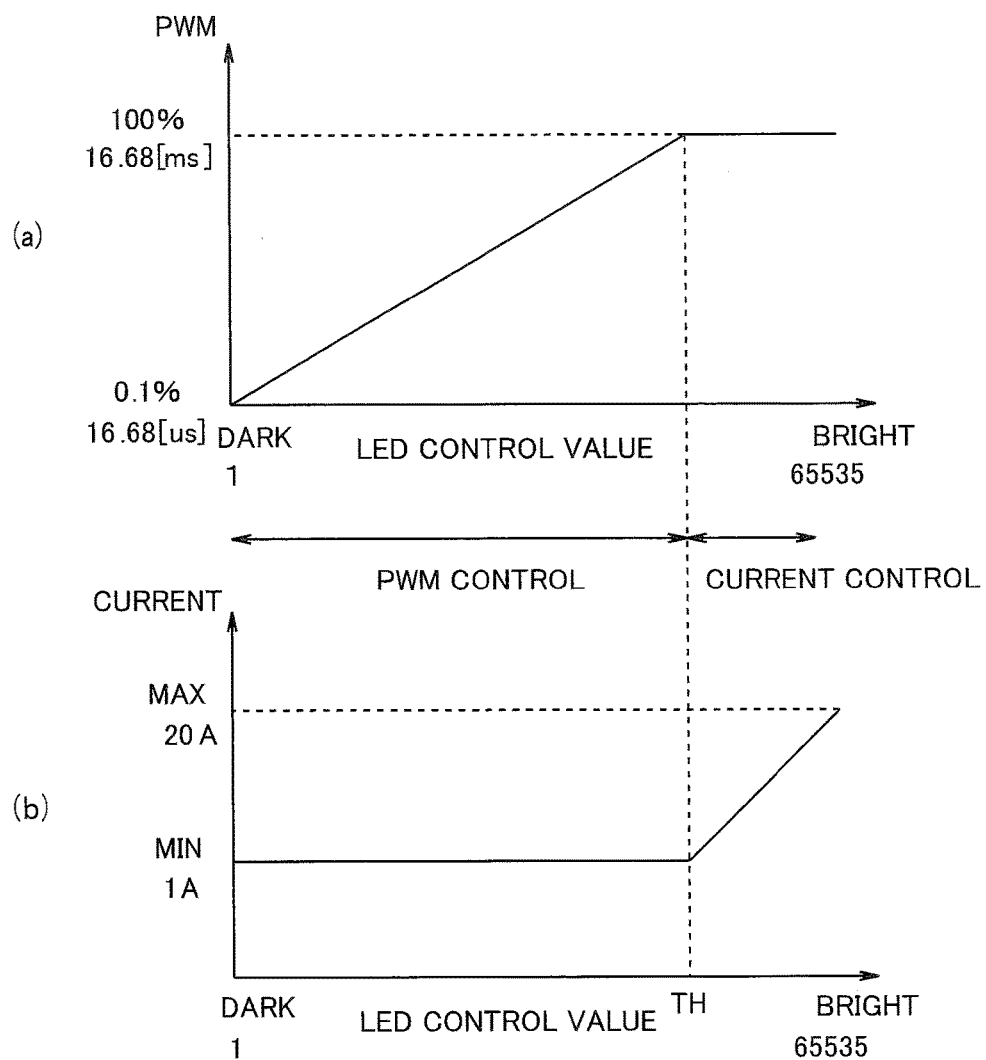
FIG. 2 includes graphs for describing an example of information stored in a memory section 53.

FIG. 2 includes graphs for describing an example of information stored in the memory section 53. FIG. 2(*a*) indicates PWM control for the G-LED 43 with the LED control value matching with the brightness control information on the abscissa axis and with the duty ratio on the ordinate axis, and FIG. 2(*b*) indicates current control for the G-LED 43 with the LED control value matching with the brightness control information on the abscissa axis and with the current value on the ordinate axis.

As illustrated in FIG. 2, the control section 41 can control the amount of light from the G-LED 43 in 65536 levels with "1" as a LED control value corresponding to a smallest amount of light from the G-LED 43 and "65535" as a LED control value corresponding to a largest amount of light. The control section 41 can control a duty ratio of PWM pulses for the G-LED 43 between 0.1% (pulse width of 16.68 μs) to 100% (pulse width of 16.68 ms), and can control the current value of the PWM pulses between 1 A, which is minimum, and 20 A, which is maximum.

As illustrated in FIGS. 2(*a*) and 2(*b*), until the duty ratio for the G-LED 43 reaches 100%, the control section 41 performs light adjustment control from an LED control value of "1", which is the darkest, to an LED control value of "TH", by varying the duty ratio with the current value set to 1 A, which is the lowest. Also, upon the duty ratio of PWM pulses reaching 100%, the control section 41 performs light adjustment control from the LED control value of "TH" to an LED control value of "65535", which is the brightest, by varying the current value from 1 A, which is minimum, to 20 A, which is maximum, with the duty ratio kept at 100%.

Upon input of the brightness control information from the video processor 20, the control section 41 reads a duty ratio and a current value corresponding to an LED control value that is based on the input brightness control information, from the table corresponding to FIG. 2, and generates light adjustment information for designating the read duty ratio and current value as light adjustment information for controlling the G-LED 43.

In the present embodiment, the control section 41 obtains respective current values to be set for the LEDs 42, 44 and 45, based on the current value set for the G-LED 43 and the scope information. Also, the control section 41 sets a duty ratio that is the same as that for the LED 43, for the LEDs 42, 44 and 45. As described above, the control section obtains light adjustment information to be set for the other LEDs 42, 44 and 45. The control section 41 outputs light adjustment information obtained for controlling the LEDs 42 to 45, to the LED drive section 46.

As described above, in the present embodiment, from the light amount that is the darkest to a predetermined light amount corresponding to a duty ratio of 100%, the control section 41 adjusts brightness by means of PWM control in which a duty ratio of PWM pulses is varied with a current amount fixed, and from the predetermined light amount corresponding to a duty ratio of 100% to a largest light amount, the control section 41 adjusts the brightness by means of current control in which the LED current is varied, with the duty ratio maintained at 100%.

Also, in the present embodiment, for all of the LEDs 42 to 45, a same pulse period of a PWM pulse, that is, a same duty ratio and a same period in which an LED current is supplied is employed. Consequently, all of the LEDs 42 to 45 are turned on simultaneously, enabling prevention of deterioration in image quality due to color balance variation even when an image of a fast-moving object is picked up. Also, pulse widths in PWM driving of the respective LEDs 42 to 45 are mutually the same, and thus, a light amount ratio among the respective LEDs 42 to 45 can be controlled only based on a current amount ratio, which facilitates the light adjustment control.

Note that although an example in which the control section 41 sets one LED 43 from among the LEDs 42 to 45 as a reference and obtains a current value for light adjustment control of the LED 43 based on the brightness control information and obtains a current value using the current value for the reference LED 43 and the ratio that is based on the scope information, for each of the other LEDs 42, 44 and 45 has been described, an LED other than the LED 43 may be set as a reference LED. Also, it is possible that information similar to that in FIG. 2 is obtained for each of LEDs according to the ratio that is based on the scope information without using a reference LED, and control values for the respective LEDs are directly read based on the brightness control information.

Note that numerical values such as current values, duty ratios and pulse lengths of pulses included in the present description are mere examples and can arbitrarily be changed.

Figure 3:
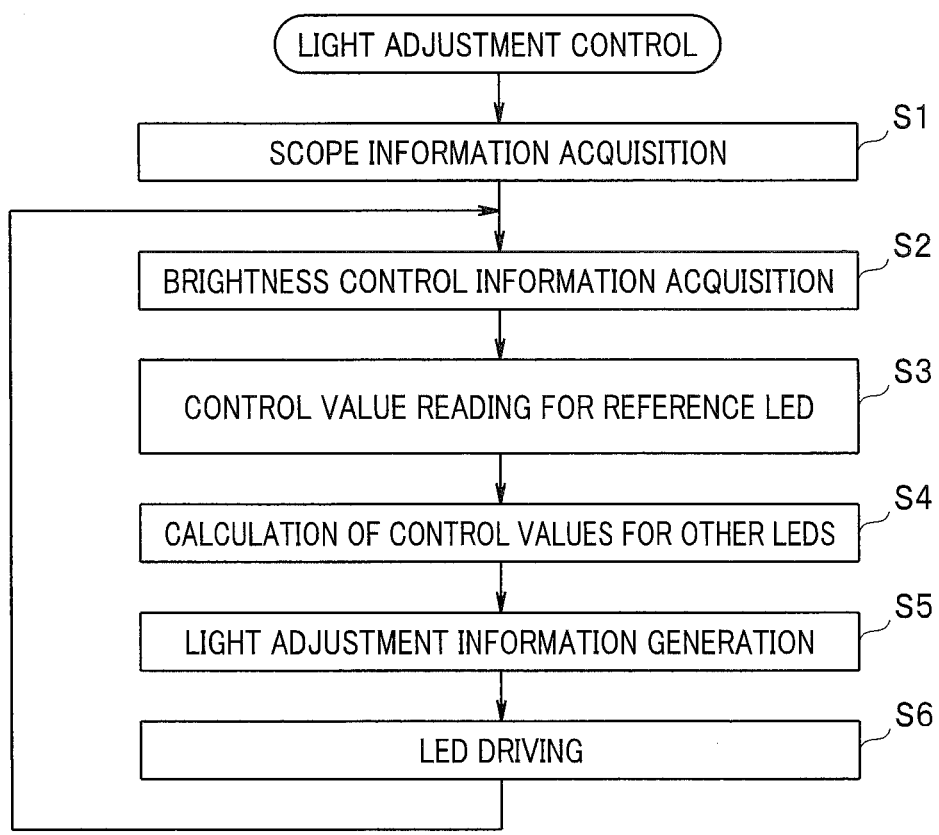
FIG. 3 is a flowchart for describing light adjustment control in the first embodiment.
Figure 4:
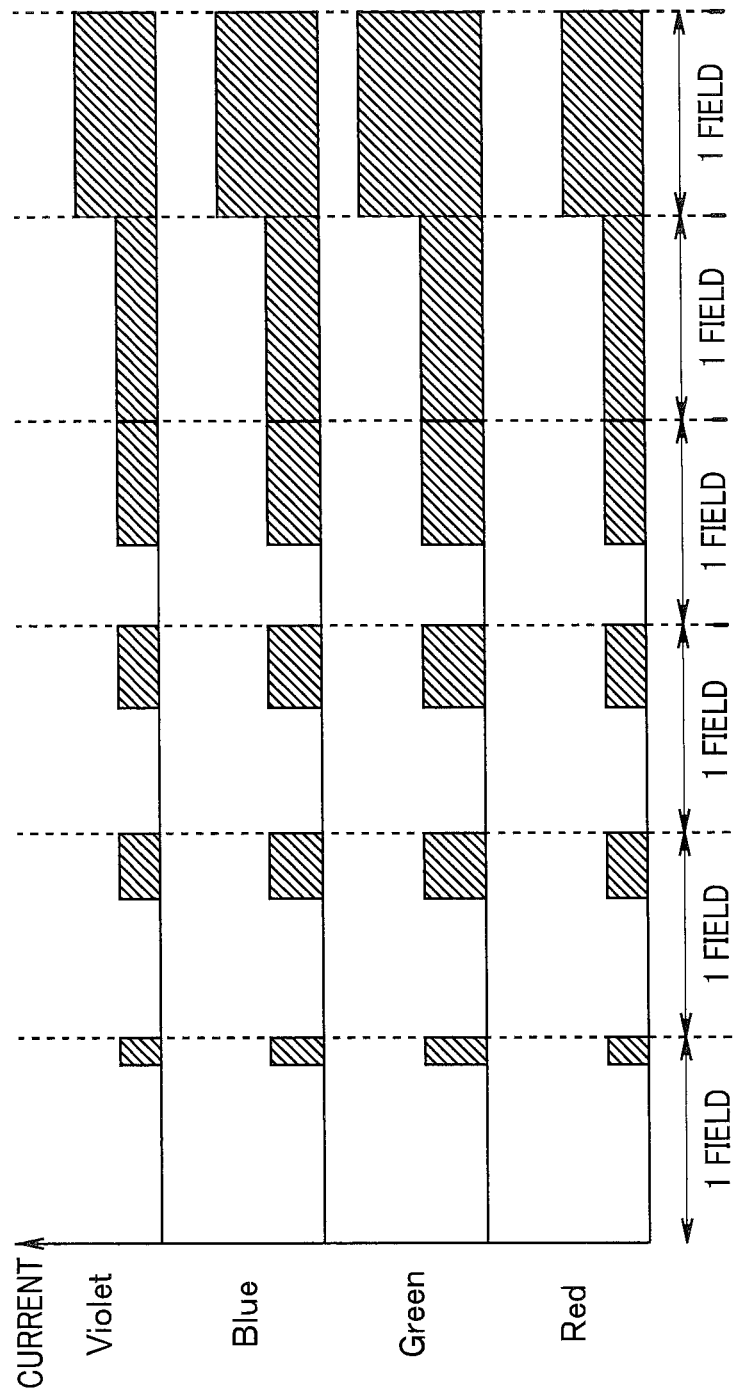
FIG. 4 is an illustrative diagram for describing drive pulses supplied to the respective LEDs 42 to 45.

Next, operation of the embodiment configured as described above will be described with reference to FIGS. 3 and 4. FIG. 3 is a flowchart for describing light adjustment control in the first embodiment. Also, FIG. 4 is an illustrative diagram for describing drive pulses supplied to the respective LEDs 42 to 45.

Upon the endoscope 10 being connected to the light source apparatus 40 via the connector 12, the reading section 51 reads the scope information stored in the storage section 19 in the endoscope 10 and outputs the scope information to the control section 41. Consequently, the control section 41 acquires the scope information (step S1). In step S2, the control section 41 acquires brightness control information from the video processor 20. The control section 41 accesses the memory section 53 based on the brightness control information and acquires control values (a current value and a duty ratio) for the G-LED 43, which is a reference LED (step S3). The control section 41 sets the current value for the LED 43 as a reference, and calculates respective current values for the other LEDs 42, 44 and 45 according to the light amount ratio that is based on the scope information (step S4).

The control section 41 generates light adjustment information for designating current values and duty ratios obtained for the respective LEDs 42 to 45 (step S5) and outputs the light adjustment information to the LED drive section 46 (step S6). The LED drive section 46 generates PWM pulses with the duty ratio and the respective current values that are based on the light adjustment information and supplies the PWM pulses to the respective LEDs 42 to 45. Consequently, the LEDs 42 to 45 produce light of amounts that are based on the light adjustment information. Beams of light emitted from the LEDs 42 to 45 are combined by the dichroic filters 47 to 49 and the resulting light enters the light guide 15 via the lens 50 as illuminating light. The illuminating light transmitted by the light guide 15 is applied to an object from the lens 14.

The image pickup device 13 receives light reflected by the object and performs photoelectric conversion of the light, thereby obtaining a picked-up image. The picked-up image is supplied to the video processor 20 via the signal wire 16. The video processor 20 subjects the picked-up image to predetermined signal processing to generate a video signal, and supplies the video signal to the monitor 30 via the cable 21. Consequently, an endoscopic image is displayed on the display screen of the monitor 30.

Also, the video processor 20 generates brightness control information by means of comparison between a brightness of the picked-up image and a target brightness. For example, the video processor 20 generates brightness control information in each one field, and outputs the brightness control information to the control section 41 in the light source apparatus 40.

Consequently, the control section 41 generates light adjustment information based on the brightness control information for, for example, each one field, to perform control so that a light amount of illuminating light formed by the combination of the light beams emitted from the LEDs 42 to 45 reaches a target brightness.

FIG. 4 indicates an example of PWM pulses supplied to the respective LEDs 42 to 45 in each field with the time on the abscissa axis. "Red", "Green", "Blue" and "Violet" in FIG. 4 indicate PWM pulses supplied to the respective LEDs 42 to 45. Each shaded part in FIG. 4 indicates a period in which an LED current is supplied, and the height of each shaded part indicates a current amount. As illustrated in FIG. 4, all of the LEDs 42 to 45 are supplied with current and thereby turned on in periods that are mutually the same. Also, the height of each shaded part matches with the light amount ratio that is based on the scope information.

Light adjustment control until the duty ratio reaches 100% from a dark state is performed by means of duty ratio control. Upon the duty ratio reaching 100%, light adjustment is performed by means of current control if the brightness of the illuminating light is further increased.

As described above, in the present embodiment, illuminating light is obtained by combining light beams emitted from a plurality of (four in FIG. 1) LEDs, enabling easy provision of illuminating light matching with spectral sensitivity characteristics of an endoscope and also enabling provision of brightness sufficient as illuminating light. Also, the respective LEDs are subjected to PWM control as well as current control, and even if it is necessary to secure a relatively-wide light adjustment range, an upper limit of the current amount can be set to be relatively low, enabling life extension of the LEDs. Also, control to turn on the respective LEDs is performed by PWM pulses having a common duty ratio, enabling provision of homogenous illumination. Also, the light amount ratio among the respective LEDs is controlled using the current amounts, enabling brightness control with the light amount ratio among the respective LEDs kept constant to be performed relatively easily. The light amount ratio among the respective LEDs is set based on spectral sensitivity characteristics of the endoscope, enabling provision of illuminating light with a desired brightness while an optimum color balance for a connected endoscope is maintained.

Second Embodiment

Figure 5:
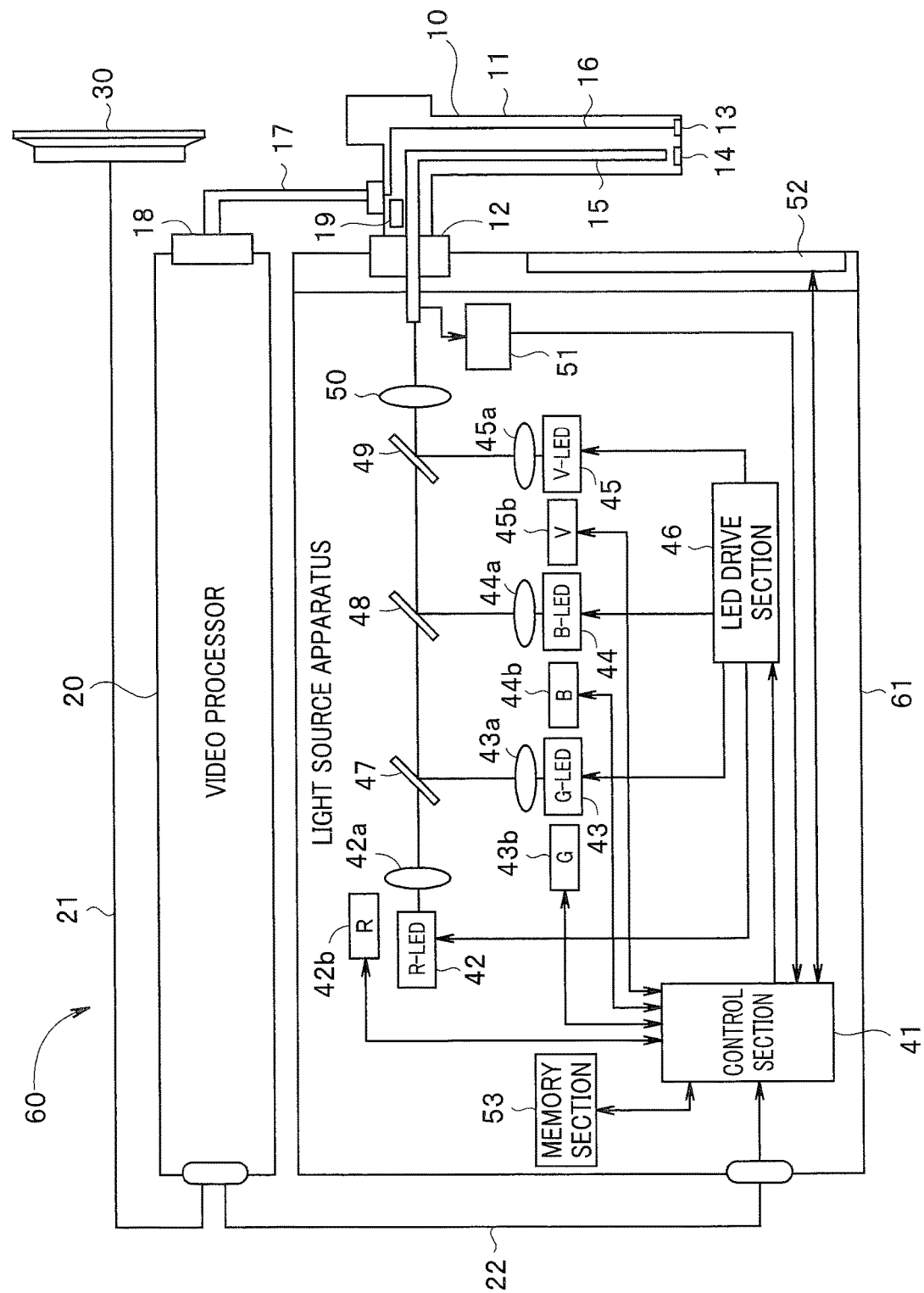
FIG. 5 is a block diagram illustrating a second embodiment of the present invention.

FIG. 5 is a block diagram illustrating a second embodiment of the present invention. In FIG. 5, components that are the same as those in FIG. 1 are provided with reference numerals that are the same as those in FIG. 1, and description thereof will be omitted. The first embodiment has been described on the premise that amounts of light from the respective LEDs 42 to 45 are proportional to respective current values. However, in reality, LEDs have temperature characteristics, and even if the LED current value is the same, the light amount varies depending on the temperature. LEDs have the property of the temperature increasing upon light emission, and thus, in order to accurately control an illuminating light amount, it is necessary to take the temperature characteristics into account. The present embodiment enables light adjustment control to be performed with a color balance maintained irrespective of such temperature characteristics.

Figure 6:
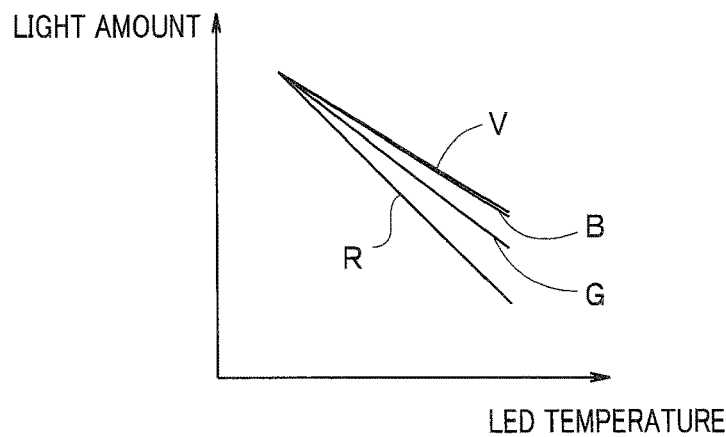
FIG. 6 is a graph with the LED temperature on the abscissa axis and the light amount on the ordinate axis, the graph indicating light amount variations where the LEDs are driven with a predetermined current value.

FIG. 6 is a graph indicating light amount variation where LEDs are driven with a predetermined constant current value, with the LED temperature on the abscissa axis and with the light amount on the ordinate axis. In FIG. 6, the characteristics of the LEDs 42 to 45 are indicated by R, G, B and V, respectively. As illustrated in FIG. 6, even if the respective LEDs are driven with a predetermined current value, an amount of light emitted by each LED varies with variation in temperature of the LED. In addition, a characteristic of the variation is different depending on the kind of the LED.

Therefore, a method in which temperatures of respective LEDs are measured to control drive currents for the respective LEDs according to the characteristics in FIG. 6 may be employed; however, LEDs are arranged relatively close to one another in a light source apparatus, and thus, it is difficult to measure variation in temperature of each single LED. Therefore, in the present embodiment, current values are controlled by obtaining amounts of light from respective LEDs.

An endoscope system 60 in FIG. 5 is different from the embodiment in FIG. 1 in that a light source apparatus 61 including photosensors 42b to 45b is employed. The photosensors 42b to 45b, which are arranged at respective positions where the photosensors 42b to 45b can detect light beams emitted by respective LEDs 42 to 45, detect amounts of light emitted by the respective LEDs 42 to 45 and output results of the detection to a control section 41. Note that the photosensors 42b to 45b are arranged at positions off respective optical paths from the respective LEDs 42 to 45 to lenses 42a to 45a.

As with in the first embodiment, the control section 41 reads information in a memory section 53 based on brightness control information, and obtains a current value and a duty ratio for a G-LED 43. In the present embodiment, the control section 41 is configured to obtain an optimum light amount ratio irrespective of temperature characteristics by correcting a light amount ratio that is based on scope information in an endoscope 10, based on the detection results from the photosensors 42b to 45b.

Figure 7:
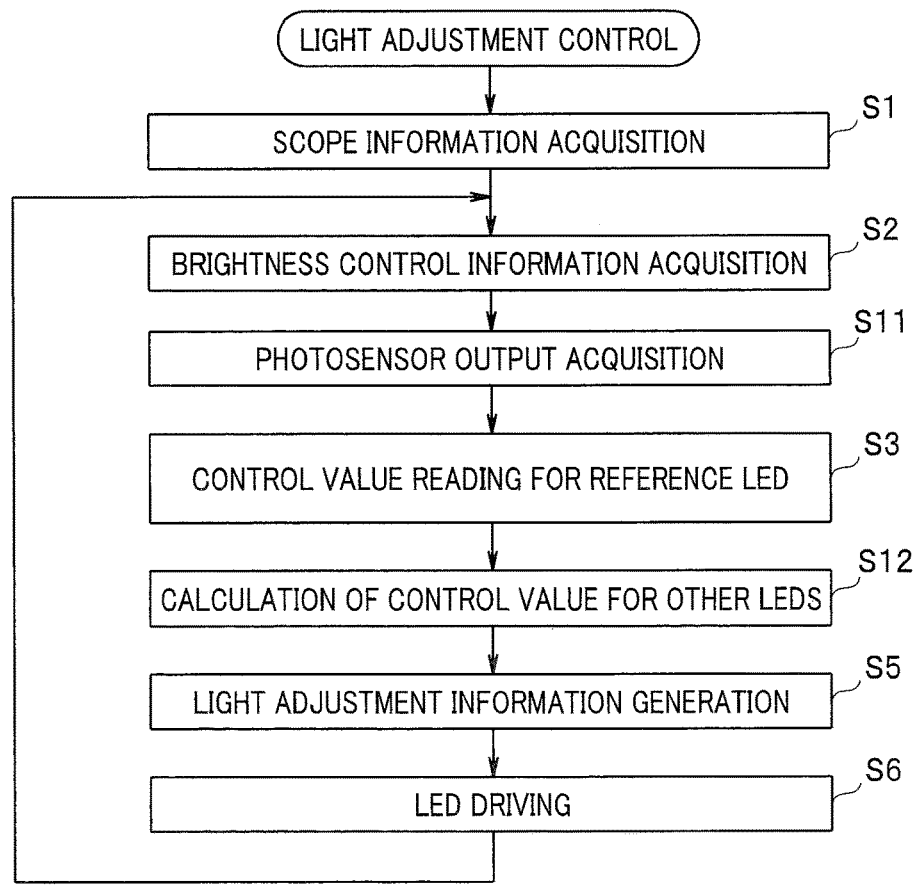
FIG. 7 is a flowchart for describing light adjustment control in the second embodiment.

Next, operation of the embodiment configured as described above will be described with reference to FIG. 7. FIG. 7 is a flowchart for describing light adjustment control in the second embodiment. In FIG. 7, steps that are the same as those in FIG. 3 are provided with reference numerals that are the same as those in FIG. 3, and description thereof will be omitted.

The present embodiment is the same as the first embodiment in that a current value and a duty ratio for a reference LED is controlled based on brightness control information. In the present embodiment, in order to prevent disruption of a color balance as a result of fluctuation in amounts of light emitted by the respective LEDs due to variation in environmental conditions such as temperature variation as mentioned above, actual amounts of light emitted by the respective LEDs 42 to 45 are monitored using the photosensors 42b to 45b and current values of drive signals to be supplied to the respective LEDs are corrected according to results of the monitoring, so as to match the amounts of light actually emitted by the respective LEDs 42 to 45 with an emitted light amount ratio set based on spectral sensitivity characteristic information stored in a storage section 19 as scope information.

The photosensors 42b to 45b detect amounts of light from the LEDs 42 to 45, respectively, and outputs results of the detection to the control section 41. In step S11 in FIG. 7, the control section 41 acquires results of detection by the photosensors 42b to 45b. The control section 41 obtains control values (a current value and a duty ratio) for a reference LED based on brightness control information (step S3). For example, the control section 41 obtains a current value and a duty ratio for the G-LED 43 in step S3.

Next, in step S12, the control section 41 obtains control values for current values to be supplied to the other LEDs based on a light amount ratio among the reference LED and the respective other LEDs that is based on the scope information, a light amount ratio among the reference LED and the respective other LEDs that has actually been obtained using the photosensors 42b to 45b, and previous control values, for the respective other LEDs.

In other words, the duty ratios of drive pulses for the other LEDs 42, 44 and 45 are made to correspond to the duty ratio for the G-LED 43 set in step 3, and the current values are increased/decreased in control periods so that the light amount ratio that is based on the scope information and the light amount ratio actually obtained using the photosensors 42b to 45b correspond to each other.

For example, if the actual amount of light from a R-LED 42 is small relative to the amount of light from the R-LED 42 according to the light amount ratio that is based on the scope information, the current value for the R-LED 43 is set so that the ratio of the LED current for the R-LED 43 to the LED current for the G-LED 43 become larger than that in a previous control period. As a result of the control section 41 obtaining the current value for the R-LED 42 using the scope information and the previous control value, the ratio of the amount of light from the R-LED 42 corresponds to the light amount ratio that is based on the scope information.

Consequently, the LED current values for the respective LEDs 42 to 45 are controlled so that the actual light amount ratio corresponds to the light amount ratio that is based on the scope information.

Note that, for example, the control section 41 may calculate amounts of correction of current values for the other LEDs 42, 44 and 45 each time light adjustment information is outputted.

The control section 41 generates light adjustment information according to the obtained current values and duty ratios, and outputs the light adjustment information to an LED drive section 46. The LED drive section 46 controls turn-on of the respective LEDs 42 to 45 based on the inputted light adjustment information. The current values for the respective LEDs are calculated based on the scope information and correction amounts according to the actual light amounts, which makes the actual amounts of light from the respective LEDs 42 to 45 match with the light amount ratio that is based on the scope information.

As described above, the present embodiment provides effects that are similar to those of the first embodiment. Also, as well as a brightness of illuminating light is controlled by controlling a brightness of a reference LED based on brightness control information, actual light amounts are measured and current values for respective LEDs are controlled so that an actual light amount ratio corresponds to a light amount ratio that is based on scope information, enabling provision of illuminating light with a desired brightness while an optimum color balance for a connected endoscope is maintained irrespective of temperature characteristics.

Third Embodiment

Figure 8:
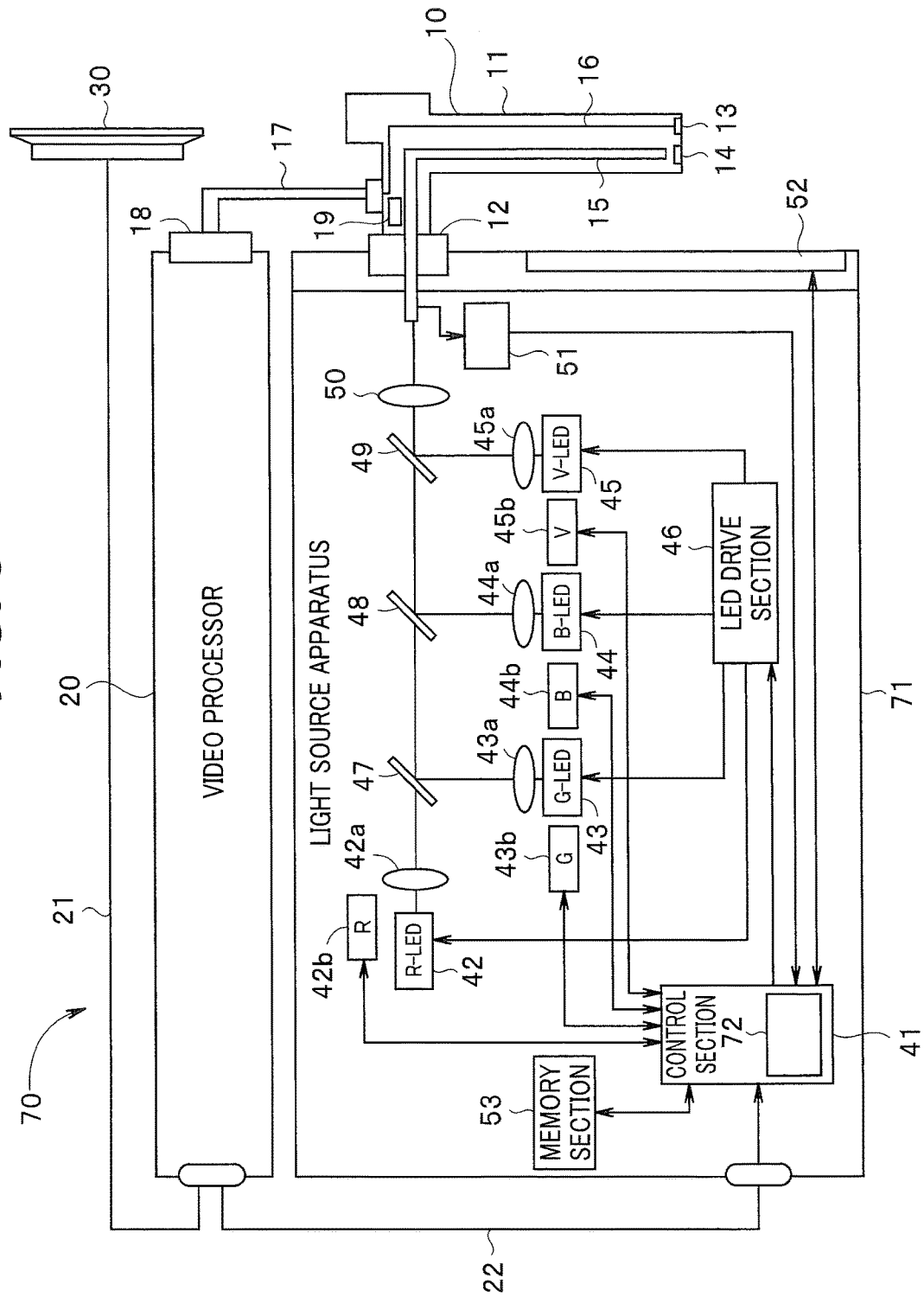
FIG. 8 is a block diagram illustrating a third embodiment of the present invention.

FIG. 8 is a block diagram illustrating a third embodiment of the present invention. In FIG. 8, components that are the same as those in FIG. 5 are provided with reference numerals that are the same as those in FIG. 5, and description thereof will be omitted. The second embodiment enables making an actual light amount ratio correspond to a light amount ratio according to scope information by measuring amounts of light from the respective LEDs 42 to 45 by means of the photosensors 42b to 45b. However, depending on the arrangement of the photosensors 42b to 45b, accurate amounts of light from the respective LEDs 42 to 45 may be unable to be measured. Therefore, the present embodiment is different from the second embodiment in that a sensing error due to, e.g., the arrangement of photosensors 42b to 45b is corrected.

Figure 9:
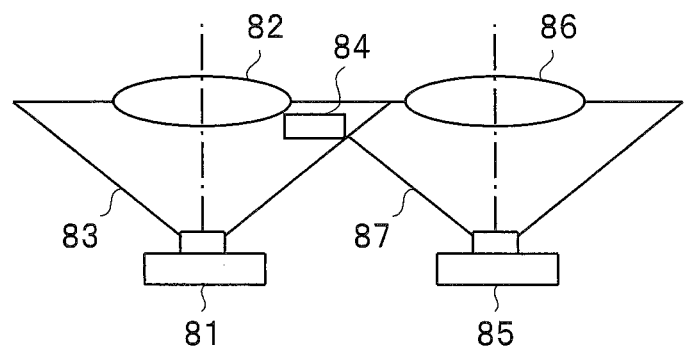
FIG. 9 includes illustrative diagrams for describing light entering photosensors 42b to 45b.
Figure 9:
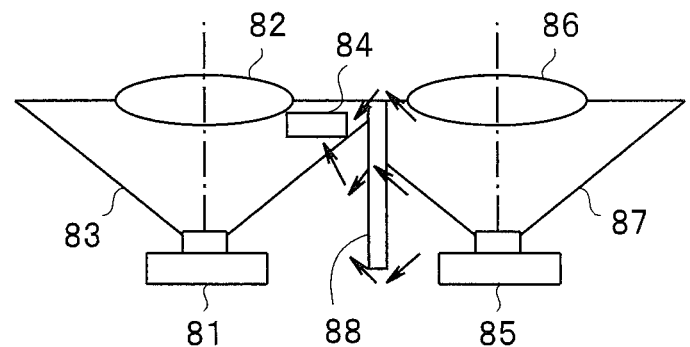

FIG. 9 is an illustrative diagram for describing light entering the photosensors 42b to 45b.

There is a demand for downsizing of endoscope light sources, and thus, it is conceivable that respective LEDs and photosensors are arranged close to one another. FIG. 9 illustrates two LEDs 81 and 85 arranged close to each other as mentioned above. On respective optical axes of the LEDs 81 and 85, lenses 82 and 86 are arranged, respectively. The lenses 82 and 86 convert light beams emitted by the LEDs 81 and 85 into substantially-parallel beams, respectively.

Within ranges 83 and 87 of the respective light beams from the respective LEDs 81 and 85, respective photosensors 84 that detect amounts of light from the respective LEDs 81 and 85 are provided. In FIG. 9, only a photosensor 84 that detects an amount of light from the LED 81 is illustrated. The photosensor 84, which is arranged within the range 83 of light emitted from the LED 81, detects light from the LED 81. However, in FIG. 9, a part of light emitted from the LED 85 also enters the photosensor 84. Thus, the photosensor 84 cannot accurately detect light emitted by the LED 81.

FIG. 9(*b*) illustrates an example in which in order to suppress sensing of light leaking from an adjacent LED, a light shielding wall 88 is arranged between the LEDs 81 and 85. However, in this case, as indicated by arrows in FIG. 9(*b*), light from the LED 85 also enter the photosensor 84 from clearance gaps around the light shielding wall 88.

As described above, if a plurality of LEDs and a plurality of photosensors are arranged in a relatively-small area, it is extremely difficult for the respective photosensors to detect accurate amounts of light from the respective LEDs, which are detection targets, respectively. Although a configuration in which photosensors each including a color filter arranged on a light-incident surface are used to allow each of the sensors to detect only light of a particular color may be employed, such configuration has the drawback of causing an increase in cost.

Therefore, in the present embodiment, a correction section that corrects detection results from photosensors 42b to 45b is provided to enhance detection accuracies of the photosensors 42b to 45b, enabling proper control of a light amount ratio among the respective LEDs 42 to 45.

An endoscope system 70 in FIG. 8 is different from the embodiment in FIG. 2 in that a light source apparatus 71 including a control section 41 with a detection result correcting section 72 added is employed. The detection result correcting section 72 corrects detection results from the photosensors 42b to 45b by means of a matrix operation. A correction matrix to be used in a matrix operation the detection result correcting section 72 performs is stored in a memory section 53. In the memory section 53, correction matrix A, which is indicated by Expression (1) below, or an inverse matrix thereof is stored.

[Expression 1]

$$A = \begin{pmatrix} a11 & a12 & \cdots & a1n \\ a21 & a22 & & \\ \vdots & & \ddots & \\ an1 & & & ann \end{pmatrix} \quad (1)$$

Correction matrix A is intended to, where n LEDs and n photosensors arranged to detect amounts of light from the n LEDs are provided in a light source apparatus, correct detection results from the n photosensors. For correction matrix A, coefficients are set, for example, before factory shipment. These coefficients can be determined based on a result of detection by each photosensor where an LED of a single color is turned on, and a result of measurement of an amount of light outputted by the apparatus. This is sequentially conducted for each of the LEDs, whereby all of coefficients in matrix A can be determined.

A coefficient ajk in correction matrix A indicates a ratio of a detection result from a k-th photosensor relative to an amount of light from a j-th LED, and for example, where only a first LED is turned on, a ratio between a detection result Sk from the k-th photosensor and a light amount LED 1 from the light source apparatus is a1k. In other words, a detection result from each photosensor is a total sum of an amount of light from a detection-target LED and amounts of light from LEDs other than the detection target (noise light), and this relationship can be indicated by the relational expression indicated in Expression (2) below.

[Expression 2]

$$\begin{pmatrix} S1 \\ S2 \\ \vdots \\ Sn \end{pmatrix} = A \cdot \begin{pmatrix} LED1 \\ LED2 \\ \vdots \\ LEDn \end{pmatrix} \quad (2)$$

The detection result correcting section 72 can acquire an amount of light from each LED with effects of amounts of light from LEDs other than the detection target removed (amount of light from the detection target LED), by means of the operation indicated by Expression (3) below, that is, an operation of multiplying detection results S from the respective photosensors by the inverse matrix of the correction matrix A.

[Expression 3]

$$\begin{pmatrix} LED1 \\ LED2 \\ \vdots \\ LEDn \end{pmatrix} = A^{-1} \cdot \begin{pmatrix} S1 \\ S2 \\ \vdots \\ Sn \end{pmatrix} \quad (3)$$

As described above, in the present embodiment, either one of correction matrix A and an inverse matrix thereof, which are intended for correcting outputs of the respective photosensors 42b to 45b, is kept in advance in the memory section 53 to perform a matrix operation, enabling detection of accurate amounts of light from the respective LEDs 42 to 45 based on detection results from the photosensors 42b to 45b. Consequently, even where LEDs and photosensors are arranged close to each other, an accurate amount of light from each LED can be detected and accurate light adjustment control of the respective LEDs can be performed so as to achieve a light amount ratio according to scope information. Other operation and effects are similar to those of the second embodiment.

What is claimed is:

1. A light source apparatus comprising:
   a first semiconductor light source that emits light with a first wavelength band;
   a second semiconductor light source that emits light with a second wavelength band that is different from the first wavelength band;
   a control section that:
      acquires information relating to a ratio of a light amount value for the light with the second wavelength band to a light amount value for the light with the first wavelength band, the information being provided for setting a light amount value for the light with the second wavelength band based on a light amount value for the light with the first wavelength band,
      obtains a light amount value for the light with the first wavelength band based on brightness control information for making a brightness of an observation image, which is generated by an endoscope for observing a subject to which the light with the first wavelength band and the light with the second wavelength band are applied, be a predetermined brightness, and,
      from the obtained light amount value for the light with the first wavelength band and the information relating to the ratio,
      determines a light amount value for the light with the second wavelength band relative to the light amount value for the light with the first wavelength band, and
      generates light adjustment information for making the first semiconductor light source and the second semiconductor light source emit light with the light amount value for the light with the first wavelength band and the light amount value for the light with the second wavelength band; and
   a drive section that, based on the light adjustment information generated by the control section, drives the first semiconductor light source and the second semiconductor light source.

2. The light source apparatus according to claim 1, wherein the control section determines a current value and a duty ratio for a drive signal for driving the first semiconductor light source, determines a duty ratio for a drive signal for driving the second semiconductor light source so as to correspond to the duty ratio for the drive signal for driving the first semiconductor light source, determines a current value for the drive signal for driving the second semiconductor light source based on the current value for the drive signal for driving the first semiconductor light source, and generates information for setting the current value and the duty ratio for the drive signal for driving the first semiconductor light source and the current value and the duty ratio for the drive signal for driving the second semiconductor light source, as the light adjustment information.

3. The light source apparatus according to claim 1, further comprising a memory section that stores the information relating to the ratio.

4. The light source apparatus according to claim 3, wherein based on a target color balance value representing a light amount balance of illuminating light emitted from the first semiconductor light source and the second semiconductor light source, the control section determines the current value for the drive signal for driving the second semiconductor light source from the current value for the drive signal for driving the first semiconductor light source.

5. The light source apparatus according to claim 4, comprising an information acquiring section that acquires the information relating to the ratio, the information being provided for obtaining the target color balance value, from the endoscope that picks up an image via an image pickup section using the illuminating light.

6. The light source apparatus according to claim 3, wherein the control section generates light adjustment information using PWM control until the duty ratio reaches 100%, and generates light adjustment information using current control upon the duty ratio reaching 100%.

7. The light source apparatus according to claim 3, further comprising a photosensor section that detects a light amount of the light emitted from the first semiconductor light source and a light amount of the light emitted from the second semiconductor light source, wherein the control section corrects the current value for the drive signal for driving the second semiconductor light source, based on results of the detection by the photosensor section.

8. The light source apparatus according to claim 7, wherein:
the photosensor section includes a first photodetection section that detects the light amount of the light emitted from the first semiconductor light source, and a second photodetection section that detects the light amount of the light emitted from the second semiconductor light source; and
the light source apparatus comprises a detection result correcting section that removes an amount of light from the second semiconductor light source that is not a target of the detection by the first photodetection section, from a result of the detection by the first photodetection section, and removes an amount of light from the first semiconductor light source that is not a target of the detection by the second photodetection section, from a result of the detection by the second photodetection section, thereby extracting only amounts of light from the first and second semiconductor light sources that are targets of the detection by the first and second photodetection sections.

9. The light source apparatus according to claim 8, comprising a second memory section that stores a correction matrix generated from the results of the detection by the first and second photodetection sections based on light from each semiconductor light source where each of the first semiconductor light source and the second semiconductor light source solely emit light,
wherein the detection result correcting section corrects the results of the detection by the first and second photodetection sections, using a matrix operation using the correction matrix.

10. The light source apparatus according to claim 1, wherein the brightness control information that the control section uses is information of a ratio between the brightness of the observation image and the predetermined brightness.

11. The light source apparatus according to claim 1, wherein the control section generates first light adjustment information for causing the first semiconductor light source to emit light with the light amount value for the light with the first wavelength band, as the light adjustment information, based on the brightness control information, and further, generates second light adjustment information for causing the drive section to drive the second semiconductor light source to emit light, from information relating to a current value of a current applied to the first semiconductor light source and the information relating to the ratio, based on the first light adjustment information.

* * * * *